US011369529B2

(12) United States Patent
Stefu et al.

(10) Patent No.: US 11,369,529 B2
(45) Date of Patent: Jun. 28, 2022

(54) SANITARY ARTICLE WITH LATERAL UNDERSURFACE RESILIENT AND DEFORMABLE PORTIONS

(71) Applicant: EasyDay Health Products Inc., Blainville (CA)

(72) Inventors: Cristian Stefu, Blainville (CA); Ioana Mihaela Hidisan, Blainville (CA); Regent Racine, Blainville (CA)

(73) Assignee: EasyDay Health Products Inc., Blainville (CA)

( * ) Notice: Subject to any disclaimer, the term of this patent is extended or adjusted under 35 U.S.C. 154(b) by 588 days.

(21) Appl. No.: 16/299,079

(22) Filed: Mar. 11, 2019

(65) Prior Publication Data

US 2019/0274900 A1  Sep. 12, 2019

Related U.S. Application Data

(60) Provisional application No. 62/641,185, filed on Mar. 9, 2018.

(51) Int. Cl.
| | |
|---|---|
| *A61F 13/15* | (2006.01) |
| *A61F 13/537* | (2006.01) |
| *A61F 13/511* | (2006.01) |
| *A61F 13/475* | (2006.01) |
| *A61F 13/514* | (2006.01) |

(52) U.S. Cl.
CPC .......... *A61F 13/537* (2013.01); *A61F 13/511* (2013.01); *A61F 13/4753* (2013.01); *A61F 13/51464* (2013.01); *A61F 2013/53773* (2013.01); *A61F 2013/53791* (2013.01)

(58) Field of Classification Search
CPC ............ A61F 13/4753; A61F 13/51464; A61F 13/539; A61F 13/505; A61F 2013/53791; A61F 2013/53773
See application file for complete search history.

(56) References Cited

U.S. PATENT DOCUMENTS

| | | | |
|---|---|---|---|
| 5,007,906 A * | 4/1991 | Osborn, III | A61F 13/511 604/385.23 |
| 6,585,712 B2 * | 7/2003 | Yoshimasa | A61F 13/47263 604/385.27 |
| 2010/0152692 A1 * | 6/2010 | Ong | A61F 13/47263 604/368 |
| 2012/0143163 A1 * | 6/2012 | Ng | A61F 13/475 604/385.101 |

* cited by examiner

Primary Examiner — Jacqueline F Stephens
(74) Attorney, Agent, or Firm — PRAXIS

(57) ABSTRACT

A sanitary article comprises a longitudinal main body defining opposite longitudinal ends and opposite lateral sides and comprising an upper part, a lower part and an absorbent core therebetween attached together at a common central portion of the longitudinal main body. The upper part and the lower part are separated from each other at the lateral sides of longitudinal main body to define separate lateral upper part and lower part portions at each of the lateral sides. The upper part comprises a liquid pervious body contacting surface. The lower part comprising a garment contacting surface.

10 Claims, 5 Drawing Sheets

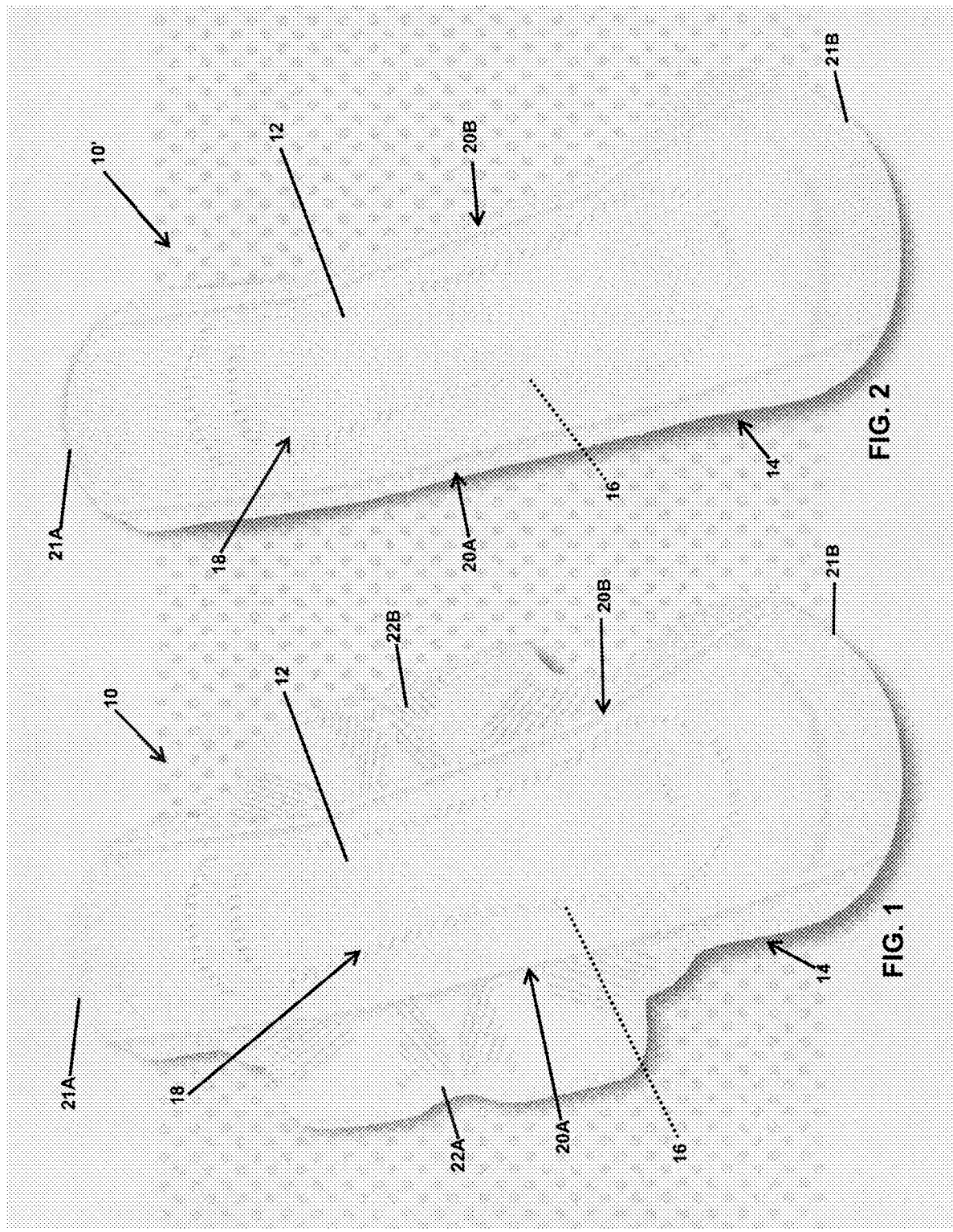

SANITARY ARTICLE WITH LATERAL UNDERSURFACE RESILIENT AND DEFORMABLE PORTIONS

CROSS-REFERENCE TO RELATED APPLICATIONS

The present application claims priority on U.S. Provisional Patent Application No. 62/641,185 filed on Mar. 9, 2018 which is incorporated herein by reference in its entirety.

TECHNICAL FIELD

The present disclosure generally relates to sanitary articles used in feminine hygiene such as sanitary napkins or pads or incontinence napkins. More particularly but not exclusively the present disclosure relates to sanitary article with lateral undersurface deformable and resilient portions.

BACKGROUND

Sanitary articles are usually disposable absorbent articles designed to be worn externally of the body by a user and to receive fluids discharged from the body. Sanitary articles are used in feminine hygiene and they include sanitary napkins or pads. Sanitary articles also include incontinence napkins. A sanitary napkin or pad is an absorbent sanitary article worn by a woman while menstruating, recovering from vaginal surgery, for lochia, after an abortion, or in any other situation where it is necessary to absorb a flow of blood from the vagina. These articles may also be used for incontinence. Of course, incontinence issues can also be managed by other sanitary articles such as incontinence napkins or pads. A sanitary article prevents soiling of the wearers clothing by such discharges. Sanitary articles include a body contacting side and a garment contacting side. Many sanitary articles have elastics on their lateral edges about the area that is in contact with the skin to act as barriers for discharged body liquid overflow. These elastic edges may often directly contact the skin of the wearer.

OBJECTS

An object of the present disclosure is to provide a sanitary article.

An object of the present disclosure is to provide a sanitary article with top and lower parts that are attached at a common central core portion and separate at lateral portions thereof.

An object of the present disclosure is to provide a sanitary article with lateral undersurface deformable and resilient portions.

SUMMARY

A sanitary article comprising: a longitudinal main body defining opposite longitudinal ends and opposite lateral sides and comprising an upper part, a lower part and an absorbent core therebetween attached together at a common central portion of the longitudinal main body, the upper part and the lower part being separated from each other at the lateral sides of longitudinal main body to define separate lateral upper part and lower part portions at each of the lateral sides; the upper part comprising a liquid pervious body contacting surface; and the lower part comprising a garment contacting surface.

In an embodiment, the lower part comprises a bottom layer defining bottom layer lateral portions at each of lateral sides.

In an embodiment, the upper part comprises a top layer and wherein the upper part portions define top layer lateral portions.

In an embodiment, the upper part lateral portions comprise respective resilient and deformable members for upwardly biasing the upper part lateral portions to prevent liquid on the body contacting surface from spilling therefrom. In an embodiment, the resilient and deformable members comprise elastics. In an embodiment, the upper part lateral portions comprise respective sheets for covering the resilient and deformable members.

In an embodiment, each of the upper part lateral portions at each of the lateral sides comprises a top layer lateral portion and a middle layer lateral portion, the top layer lateral portion overlying the middle layer lateral portion and defining a space therebetween, the middle layer lateral portion overlying the lower part lateral portion and defining a space therebetween. In an embodiment, each of the middle layer portions comprises a respective resilient and deformable member for upwardly biasing a respective top layer lateral portion to prevent liquid on the body contacting surface from spilling therefrom. In an embodiment, the resilient and deformable members comprise elastics. In an embodiment, the middle layer lateral portions comprise respective sheets for covering the resilient and deformable members.

In an embodiment, the garment contacting surface is liquid impervious.

In an embodiment, the garment contacting surface comprises adhesive for adhering an undergarment of a user.

In an embodiment, the lower part comprises laterally extending wings for being wrapped around an undergarment of a user.

In accordance with an aspect of the present disclosure, there is provided a sanitary article comprising: a longitudinal main body defining opposite ends and opposite lateral sides and comprising a liquid pervious body contacting surface, an opposite liquid impervious garment contacting surface and an absorbent core therebetween; a resilient and deformable portion positioned on the main longitudinal body at each lateral side of the longitudinal main body; and an edge portion laterally extending from the longitudinal main body and overlaying the resilient and deformable portion thereby preventing direct contact between the resilient and deformable portion and a user's skin, wherein the resilient and deformable portion at each lateral side of the longitudinal main body imparts a concave shape to the body contacting surface for maintaining body liquid discharge thereon.

In an embodiment, the concave shape of the body contacting surface provides a space between at least a portion of the body contacting surface and a user's body.

In an embodiment, the sanitary article further comprises a top sheet defining the body contacting surface and backing sheet defining the garment contacting surface. In an embodiment, the top and backing sheets define at a junction thereof at each lateral side of the longitudinal main body a lateral junction sheet. In an embodiment, the lateral junction sheet at each lateral side of the longitudinal main body comprises the resilient and deformable portion. In an embodiment, the edge portion at each lateral side of the longitudinal main body extends from the top sheet and defines a top surface for being in contact with a user's skin and an opposite undersurface for contacting the resilient and deformable portion.

In an embodiment, the resilient and deformable portion at each lateral side of the longitudinal main body is upwardly biased relative to the body contacting surface. In an embodiment, the resilient and deformable portion at each lateral side of the longitudinal main body defines a respective lateral wall about the body contacting surface.

In an embodiment, the garment contacting surface comprises an adhesive material for adhering to at least a portion of an undergarment worn by a user.

In an embodiment, the sanitary article further comprises wings extending from each lateral side of the longitudinal main body. In an embodiment, the wings comprise an adhesive substance for adhering to at least a portion of an undergarment worn by a user.

In an embodiment, the resilient and deformable portion comprises elastic.

Other objects, advantages and features of the present disclosure will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 1 is a top view of the sanitary article in accordance with a non-restrictive illustrative embodiment of the present disclosure;

FIG. 2 is a top view of the sanitary article in accordance with another non-restrictive illustrative embodiment of the present disclosure;

DETAILED DESCRIPTION OF ILLUSTRATIVE EMBODIMENTS

Figure 3:
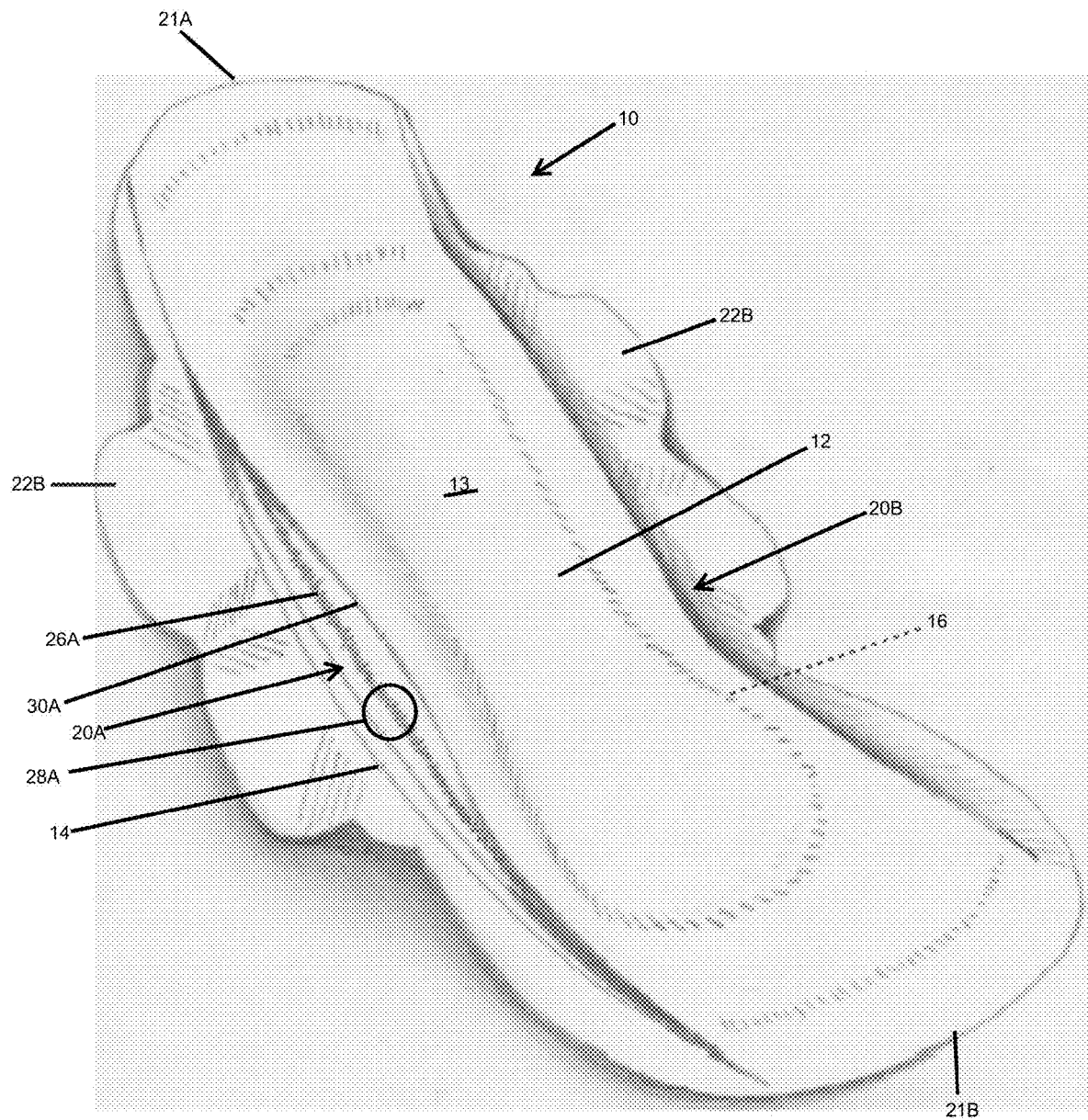
FIG. 3 is a top and lateral side, perspective view of the sanitary article of FIG. 1 in accordance with a non-restrictive illustrative embodiment of the present disclosure.

Generally stated and in accordance with an aspect of the present disclosure, there is provided a sanitary article comprising a longitudinal main body defining opposite longitudinal ends and opposite lateral sides and comprising an upper part, a lower part and an absorbent core therebetween attached together at a common central portion of the longitudinal main body. The upper part and the lower part are separated from each other at the lateral sides of longitudinal main body to define separate lateral upper part and lower part portions at each of the lateral sides. The upper part comprises a liquid pervious body contacting surface. The lower part comprising a garment contacting surface.

In an embodiment, each of the upper part lateral portions at each of the lateral sides comprises a top layer lateral portion and a middle layer lateral portion. The top layer lateral portion overlies the middle layer lateral portion and defines a space therebetween. The middle layer lateral portion overlies the lower part lateral portion and defines a space therebetween. In an embodiment, each of the middle layer portions comprises a respective resilient and deformable member for upwardly biasing a respective top layer lateral portion to prevent liquid on the body contacting surface from spilling therefrom. In an embodiment, the lower part comprises a bottom layer defining bottom layer lateral portions at each of lateral sides.

Generally stated and in accordance with an aspect of the present disclosure, there is provided a sanitary article comprising a longitudinal main body defining opposite ends and opposite lateral sides and comprising a liquid pervious body contacting surface, an opposite liquid impervious garment contacting surface and an absorbent core therebetween. A resilient and deformable portion is positioned on the main longitudinal body at each lateral side of the longitudinal main body. An edge portion laterally extends from the longitudinal main body overlaying the resilient and deformable portion thereby preventing direct contact between the resilient and deformable portion and a user's skin. The resilient and deformable portion at each lateral side of the longitudinal main body imparts a concave shape to the body contacting surface for maintaining body liquid discharge thereon.

FIG. 1 shows the sanitary article 10, including a top sheet 12, a backing sheet 14 and core 16 therebetween. The top sheet 12 is liquid pervious and defines the body contacting side or surface of the sanitary article 10. The backing sheet 14 is liquid impervious thereby acting as a protective barrier. The backing sheet 14 defines the garment (or undergarment) contacting side or surface and adheres to the wearer's undergarment via an adhesive. Adhesives such as pressure sensitive adhesives are suitable for this purpose. The core 16 is an absorbent core that absorbs discharge. In an embodiment the body contacting surface of the sanitary article 10 may also include an adhesive to adhere to the body of the user.

The top sheet 12 is made of materials which are compliant and readily conform to the shape of the body. The top sheet 12 may exhibit good strikethrough and rewet characteristics, permitting bodily discharges to rapidly penetrate therethrough to the core 16, but not flow back to the skin of the wearer. The top sheet 12 may be porous to permit discharged liquids to pass through to the core 16. The body contacting surface provides comfortable and dry-feeling contact with body surfaces while allowing free passage of fluids therethrough into the absorbent core 16.

The backing sheet 14 prevents discharges absorbed by the core 16, from escaping. The backing sheet 14 prevents the fluids which are expelled, or which escape from the absorbent core 16 from soiling the user's garments.

The absorbent core 16 is intermediate the top sheet 12 and the backing sheet 14 and the article 10 is integrally or unitarily assembled. Therefore, the body contacting surface of the article 10 is defined by the top sheet 12 and the opposite protective barrier or garment contacting surface is defined by the backing sheet 14. The absorbent core 16 has two opposed faces, one oriented towards the backing sheet 14 and one oriented towards the top sheet 12. The absorbent core 16 provides for receiving, collecting and containing bodily discharges such as menses, deposited thereon or which pass through the top sheet 12. In an embodiment, the core 16 is configured to be narrow and thin so as to be comfortable to the wearer.

The article 10 defines a longitudinal main body 18 comprising the top sheet 12, the backing sheet 14 and the absorbent core 16. The main body 18 is delimited by opposite lateral sides or margins 20A and 20B and opposite ends 21A and 21B. The opposite lateral margins 20A and 20B run along the longitudinal length of the main body 18. The opposite lateral margins 20A and 20B define the width of the body portion 18 whereas the ends 21A and 21B define the length of the body portion 18.

A pair of wings or flaps 22A and 22B may extend beyond each margin 20A and 20B, respectively. The wings 22A and 22B may extend along the longitudinal length of each margin 20A and 20B. The wings 22A and 22B may be contiguous with the backing sheet 14, contiguous with the top sheet 12 or a laminate of both the top sheet 12 and the backing sheet 14. Each wing 22A and 22B has a garment contacting face or portion that contacts the wearer's undergarments in use which may also include an adhesive material. The wings 22A and 22B may be provided in a variety of suitable shapes and when in use extend beyond the undergarment crotch portion to be flipped thereunder and adhered to the outer surface of the undergarment opposite the body contacting surface thereof.

Alternatively, FIG. 2 shows a sanitary article 10' which is similar to article 10 in all but the lack of wings 22A and 22B. As such, the description of sanitary article 10 herein applies to sanitary article 10' mutatis mutandis.

Figure 4:
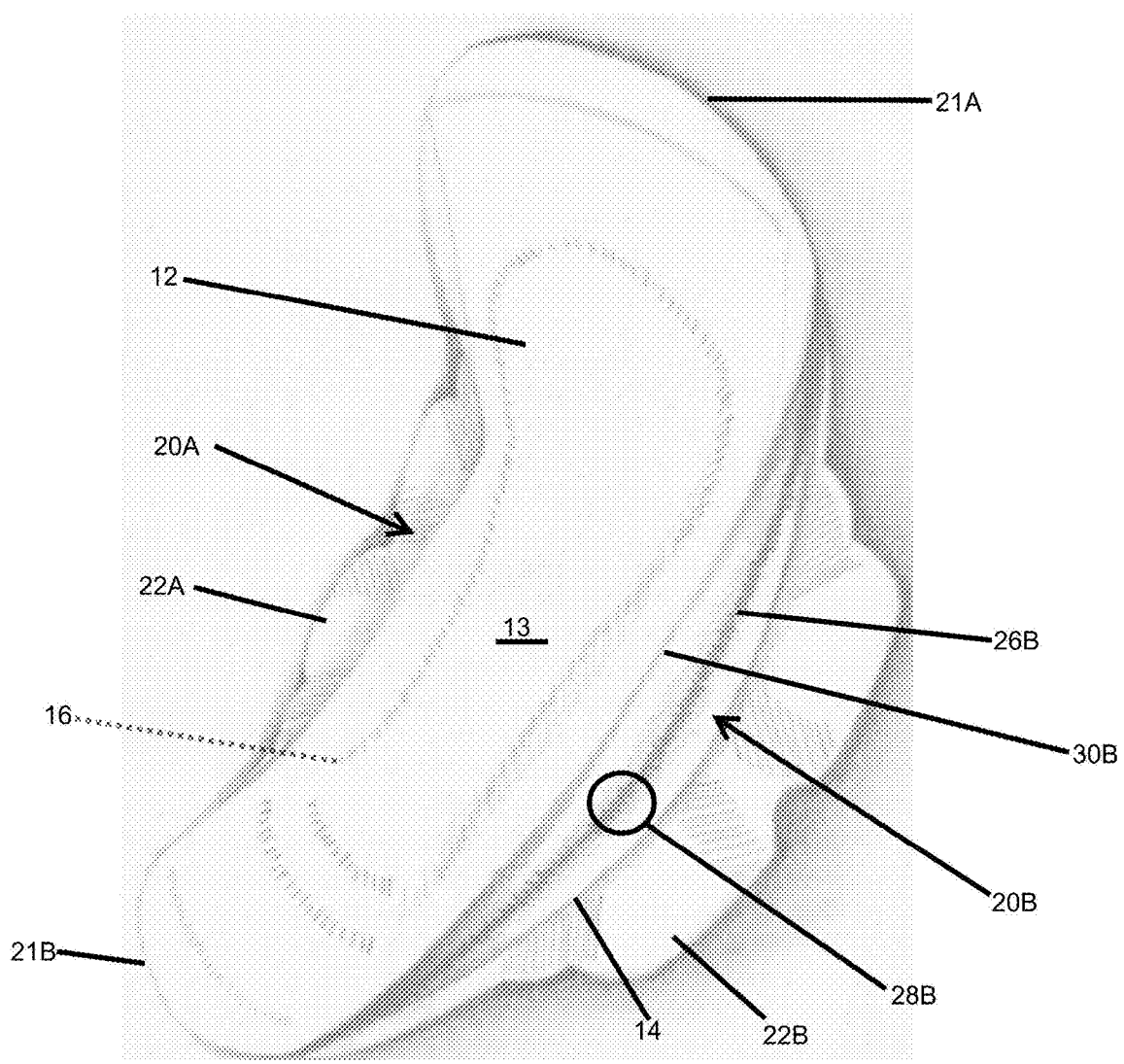
FIG. 4 is a top and perspective view of the sanitary article of FIG. 1 in accordance with a non-restrictive illustrative embodiment of the present disclosure, the lateral side shown being opposite to the lateral side of FIG. 3
Figure 5:
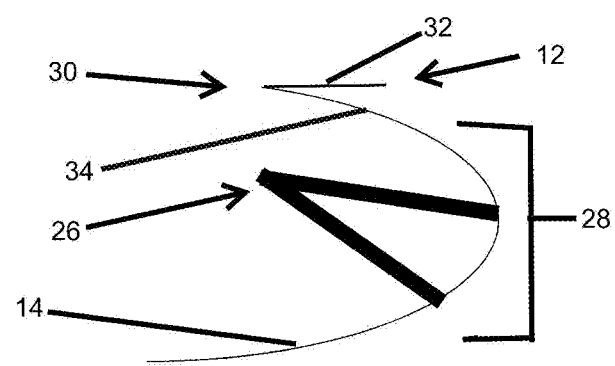
FIG. 5 is a schematic sectional representation of a given lateral side of the sanitary article of FIG. 1 in accordance with a non-restrictive illustrative embodiment of the present disclosure.

Turning now to FIGS. 3-5, the margins 22A and 22B include respective resilient and deformable portions 26A and 26B. The resilient and deformable portions 26A and 26B run along a length of each respective margin 22A and 22B.

Turning to FIG. 5, a given deformable and resilient portion, generally denoted as 26, is located about a lateral junction of the top sheet 12 and the backing sheet 14. A sheet at this lateral junction, generally denoted as 28, defines the sheet area between the adjoined top and backing sheets 12 and 14, respectively, and acts as a lateral wall enclosing the absorbent core 16 therein. The lateral junction sheet 28 may be adjoined to the absorbent core 16.

With reference to FIGS. 3 and 4, the article 10 includes lateral junction sheets 28A and 28B at each margin 20A and 20B, respectively.

As show, in FIGS. 3 to 4, the main body 18 defines laterally extending edge portions 30A and 30B at each margin 20A and 20B, respectively. In the example herein, the edge portions 30A and 30B are defined by the laterally extending edges of the top sheet 12. In FIG. 5, an edge portion is generally denoted at 30. The edge portions 30A and 30B are each contiguous with a respective lateral junction sheet 28A and 28B. The edge portions 30A and 30B define respective top surfaces 32 and undersurfaces 34. The edge portions 30A and 30B respectively overlay the resilient and deformable portions 26A and 26B, with the undersurfaces 34 engaging the portions 26A and 26B. The skin of the wearer is in contact with top surfaces 32 of the edge portions 30A and 30B so that the skin of the wearer does not touch the portions 26A and 26B. As such, the edge portions 30A and 30B act as a barrier between the skin of the user and the portions 26A and 26B.

The resilient and deformable portions 26A and 26B may comprise elastic, or a mixture of elastic and other suitable materials, or other suitable materials without necessarily being elastic as can be contemplated by the skilled artisan. The resilient and deformable portions 26A and 26B are upwardly biased in such a way as to form with the edge portions 30A and 30B side walls along the margins 20A and 20B acting as lateral barriers about the sides of the top sheet's body contacting surface 13. The resilient and deformable portions 26A and 26B provide tension to the main body 18 causing it to take a concave shape or a cup-like shape. More particularly the resilient and deformable portions 26A and 26B impart a concave shape to at least a portion of the body contacting surface 13 for maintaining body liquid discharge thereon.

The above-mentioned lateral barriers about the sides of the body contacting surface 13 together with the concave shape of at least a portion of the body contacting surface 13 (and the main body 18) allow extra time to the top sheet 12 for liquid to pass therethrough as well as additional time for the absorbent core 16 to absorb this discharge. Moreover, the above-mentioned lateral barriers about the sides of the top surface 13 together with the concave shape of at least a portion of the body contacting surface 13 (and the main body 18), maintain liquid on and prevent it from spilling past margins 20A and 20B or ends 21A and 21B.

Since the resilient and deformable portions 26A and 26B are beneath the edge portions 30A and 30B, they will not be in contact with the skin, they can therefore achieve the above without discomfort to the user. In this way, the resilient and deformable portions 26A and 26B will not irritate, scratch or cut the skin of the user. Moreover, the top surfaces 32 are made of comfortable material with a soft feel on the user's skin.

Since the resilient and deformable portions 26A and 26B are beneath the edge portions 30A and 30B and are not in contact with the skin of the user, the material used for portions 26A and 26B can be stronger, more robust, thicker, have higher tension. The foregoing provides for a more pronounced concave shape of the main body 18 along with thicker, higher, or stronger side barriers for the body contacting surface 13. The foregoing provides from using a thinner overall main body 18, including a thinner absorbent core 16 and or a thinner top sheet 12 and or a thinner backing sheet 14. Of course, thicker article 10 can also be used.

The concave shape of at least a portion of the body contacting surface 13 provides for a space between at least a portion of the body contacting surface 13 and body of the user. The foregoing space provides for air flow rendering the materials of the article 10 more breathable.

Since the margins 20A and 20B are lifted upwardly toward the wearer in order to keep liquid in, air flow is also increased rendering the materials of article 10 more breathable.

The resilient and deformable portions 26A and 28B, keep the liquid from not pouring from the sides or margins 20A and 20B and since they are under the top sheet 12 or the top sheet 12 and a respective wing 22A or 22B, they are not in contact with the skin of the user.

Figure 6:
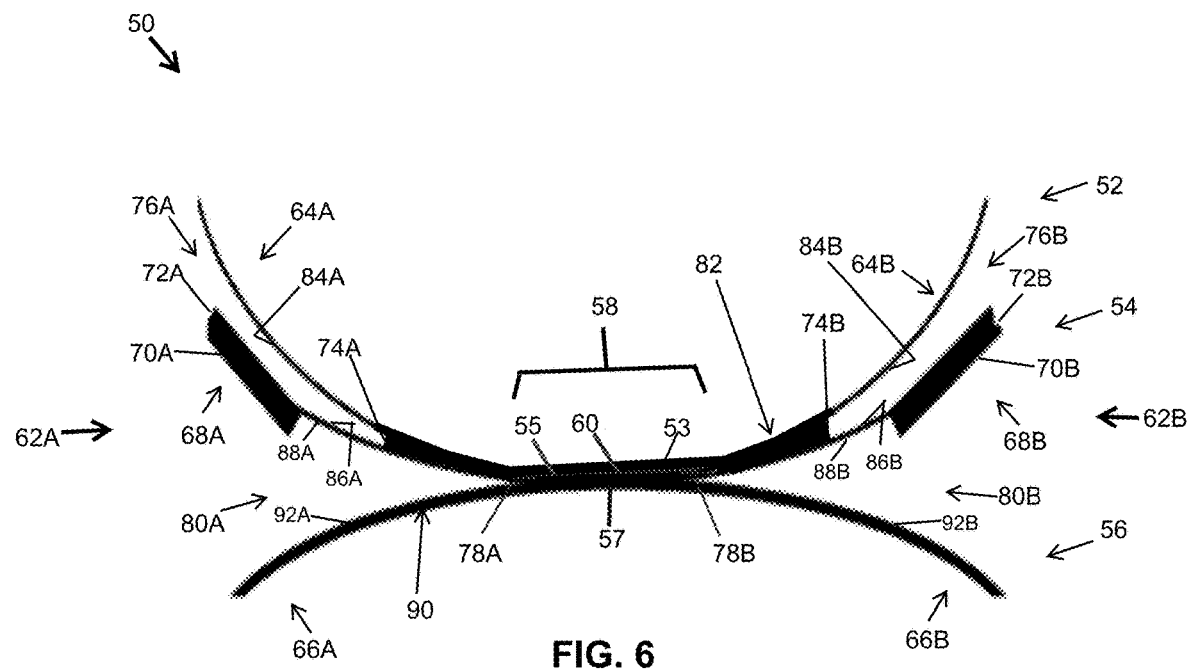
FIG. 6 is schematic cross-sectional representation of the sanitary article of FIG. 7 taken along line 6-6 thereof, in in accordance with a non-restrictive illustrative embodiment of the present disclosure.

FIG. 6 shows is a schematic front cross-sectional representation of the sanitary article 50 as fully shown in FIGS. 7 and 8 which will provide further clarity to the description of FIGS. 7 to 10 further below. The schematic front cross-sectional representation of FIG. 6 is schematically taken along line 6-6 of FIG. 7. FIG. 6 represents the sanitary article 50 when in use and interposed between the body of a user and their undergarment.

The sanitary article in the form of a multilayered laminate sanitary napkin comprising a top layer 52, a middle layer 54 and a bottom layer 56. The layers 52, 54, and 56 are attached together at a central core portion 58 which includes the absorbent core layer 60 of the napkin 50 providing unattached loose lateral layer portions (64A, 64B, 66A, 66B, 68A, 66B) at each lateral side 62A and 62B of the attached laminated central portion core portion 58. It will be understood by the skilled artisan that layers 52, 54, 56 as well as the absorbent core layer 60 are comprised of one or more layers thus providing the multilayered laminate structure of the sanitary napkin 50.

The top layer 52 comprises a central part 53 thereof that forms part of the laminate central core portion 58 and two lateral portions 64A and 64B that are unattached to layers 54 and 56. The middle layer 54 comprises a central part 55 thereof that forms part of the laminate central core portion 58 and two lateral portions 68A and 68B that are unattached to layers 52 and 56. The bottom layer 56 comprises a central part 57 thereof that forms part of the laminate central core portion 58 and two lateral portions 66A and 66B that are unattached to layers 52 and 54.

Thus, each lateral side 62A and 62B of the napkin 50 provides three separate lateral layer portions (64A, 64B, 66A, 66B, 68A, 66B). More specifically, lateral side 62A includes a top lateral layer portion 64A, a bottom lateral layer portion 66A and a middle lateral layer portion 68A interposed between the top and bottom lateral layer portions 64A and 66A, respectively. Similarly, lateral side 62B includes a top lateral layer portion 64B, a bottom lateral layer portion 66B and a middle lateral layer portion 68B interposed between the top and bottom lateral layer portions 64B and 66B respectively. The top lateral layer portions 64A and 64B engage the body of the user. The bottom lateral layer portions 66A and 66B adhesively engage the undergarment of the user. The middle lateral layer portions 68A and 66B have respective resilient and deformable members 70A and 70B at their free end sections 72A and 72B respectively. In an embodiment, the resilient and deformable members 70A and 70B are elastics.

Each top lateral layer portion 64A and 64B respectively loosely overlies a respective middle lateral layer portion 68A and 68B. Therefore, the top lateral layer portions 64A and 64B cover the elastic 70A and 70B preventing them from touching the skin of the user. The elastics 70A and 70B are upwardly biased and thus upwardly bias the top lateral layer portions 64A and 64B providing a concave like configuration to the layers 52 and 54. The top and middle layer portions 64A and 68A, respectively, at lateral side 60A are separate portions that meet at an inwardly recessed junction 74A near central core portion 58 and that define a space 76A therebetween. The top and middle layer portions 64B and 68B, respectively, at lateral side 60B are separate portions that meet at an inwardly recessed junction 74B near central core portion 58 and that define a space 76B therebetween.

Each middle lateral layer portion 68A and 68B respectively and loosely overlies a respective bottom lateral layer portion 66A and 66B. The middle and bottom layer portions 68A and 66A, respectively, at lateral side 60A are separate portions that meet at an inwardly recessed junction 78A near central core portion 58 and that define a space 80A therebetween. The middle and bottom layer portions 68B and 66B, respectively, at lateral side 60B are separate portions that meet at an inwardly recessed junction 78B near central core portion 58 and that define a space 80B therebetween.

The bottom layer lateral portions 66A and 66B are adhesively attached to the undergarment and therefore are downwardly biased providing a convex shape to the bottom layer 56.

Thus, the three lateral layer portions at each side 60A (namely portions 64A, 68A, 66A) and 60B (namely portions 64B, 68B, 66B) are independent and separate from one another as the layers 52, 54, and 56 are only attached at the central core portion 58 of the sanitary napkin 50. Therefore, the downward bias of the attached bottom layer lateral portions 66A and 66B does not affect the upward bias of the middle (68A, 68B) or top (64A, 64B) lateral layer portions. The foregoing provides lateral sides 60A and 60B of the napkin 50 that are more mobile and more flexible. Moreover, the space (80A, 80B) between the middle layer lateral portions (68A, 68B) and the bottom layer lateral portions (66A, 66B) and the space (76A, 76B) between the top layer lateral portions (64A, 64B) and the middle layer lateral portions (68A, 68B) provides the napkin 50 to breath at each lateral side 60A, 60B.

The top layer 52 defines a body contacting side 82. The lateral portions of the 64A and 64B of the top layer 52 define respective underside surfaces 84A and 84B that engage the elastics 70A and 70B.

The middle layer lateral portions 68A and 68B define respective top surfaces 86A and 86B and opposite respective undersurfaces 88A and 88B between their respective elastic 70A or 70B and the junction 74A or 74B. The bottom layer 54 defines a garment engaging outer surface 90 and inner surfaces 92A and 92B at each respective lateral side 62A and 62B. Middle layer Surfaces 88A and 88B respectively engage surfaces bottom layer surfaces 92A and 92B.

The concave shape of the top layer 52 due to the upwardly biasing elastics 70A and 70B provides for keeping body discharge such as menses, blood, urine on the body contacting inner face 82 to be absorbed by the absorbent core 60. The top lateral layer portions 64A and 64B protect the user's skin from the elastics 70A and 70B. The role of the middle lateral portions 68A and 68B and of the elastics 70A and 70B is to life up the lateral portions 64A and 64B and to pull the longitudinal ends of the sanitary napkin 50 inwardly in order to create a cup-like shape as shown in FIGS. 7 and 8 (which will be discussed hereinbelow). The V-shape of the lateral sides 60A and 60B formed by portions 64A, 68A, 64B, 68B provides breathability further increasing comfort.

The bottom layer 56 comprises an adhesive on its garment engaging outer face 90 which is covered by a removable film when not in use. As such, the bottom layer 56 will be adhered onto the underpants and be wrapped around defining a convex shape as schematically represented in FIG. 6. In an embodiment, the bottom layer 56 is a protective plastic layer that will maintain the liquid that seeps through layers 52 and 54 from contacting the undergarment. Layer 56 provides for maintaining the accumulated liquid within the absorbent core 60 and not seeping through at central core portion 58.

The absorbent core 60 is positioned between the body contacting inner face 82 and the garment engaging outer face 90.

The convex shape of the bottom layer 56 when mounted to a garment does not affect the cup and concave shape of the top layer and middle layers 52 and 54 and vice versa. This cup and concave shape of layers 52 and 54 allow for keeping liquid on side 80 and the convex shape of layer 56 allows for a better attachment to the garment due to the detached lateral sides 60A and 60B described herein. Moreover, the top part 92 of the napkin which comprises layers 52 and 54 moves with the user's body, taking the shape of the body thereby increasing comfort for the user while the lower part of the napkin 50 defined by the bottom layer 56 stays attached to the undergarment.

Turning now to the FIGS. 7 to 10 the sanitary napkin 50 constructed as per the configuration schematically represented in FIG. 6 will be further described. The following description will refer back to FIG. 6 when discussing FIGS. 7 to 10.

The sanitary napkin 50 defines a main body 100 having lateral sides 62A and 62B, longitudinal ends 102A and 102B, an inner body contacting side 82 defined by the top layer 52 which is a liquid pervious layer for allowing liquid to pass through to the absorbent core 60. The bottom layer 56 is a liquid impervious layer for keeping the liquid from passing from the absorbent core 60 to the undergarment and clothes of the user.

The absorbent core 60 is interposed between top and bottom layers 52 and 56 and between junctions 74A and 78A and middle layer lateral portion 68A at lateral side 62A and junctions 74B and 78B and middle layer lateral portion 68B at lateral side 62B. The portions 53, 55, 57 and the absorbent core 60 are all attached together forming a single central core portion 58.

In an embodiment, the middle layer 54 does not include a central portion 55 thereof and is simply a lateral structure formed between layers 52 and 56 and therefor comprises portion 68A interconnected with junctions 74A and 78A and portion 68B interconnected with junctions 74B and 78B.

The bottom layer 56 comprises a pair of wings 104A and 104B extending from the main body at each lateral side 62A and 62B. The wings 104A and 104B are wrapped around the undergarment as is known in the art which provide the convex shape to layer 56 schematically shown in FIG. 6.

The main body 100 defines along its longitudinal length front and rear body sections 106A and 106B, respectively with a pad section 108 interposed therebetween and comprising the absorbent core 60.

Figure 7:
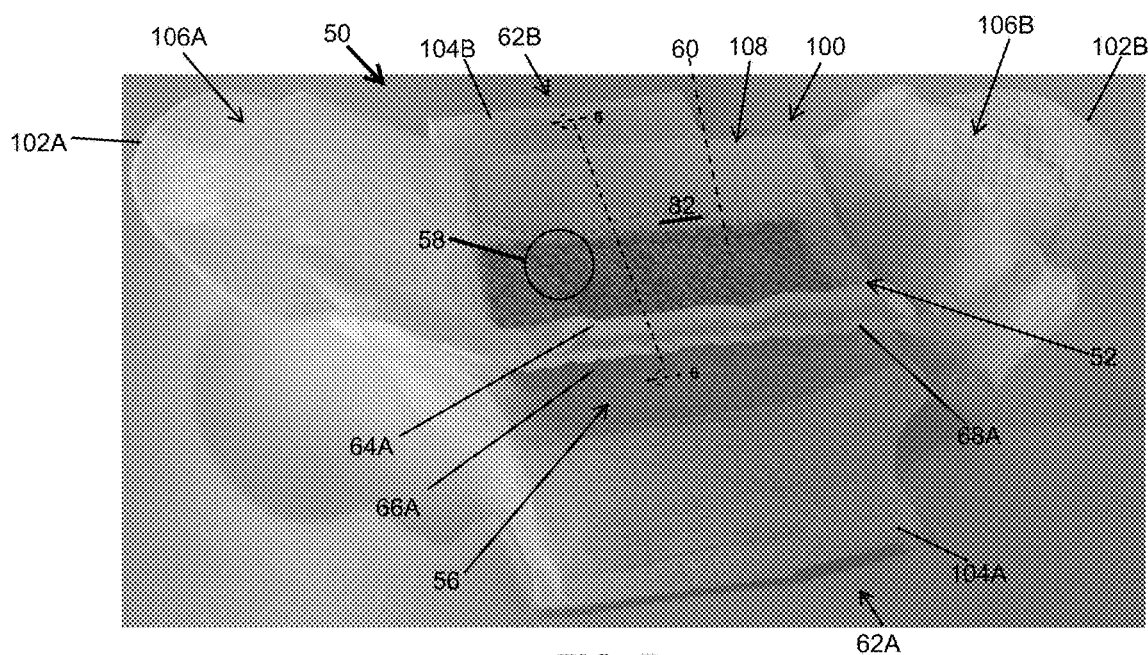
FIG. 7 is a top and lateral side perspective view of a sanitary article in accordance with a non-restrictive illustrative embodiment of the present disclosure.
Figure 8:
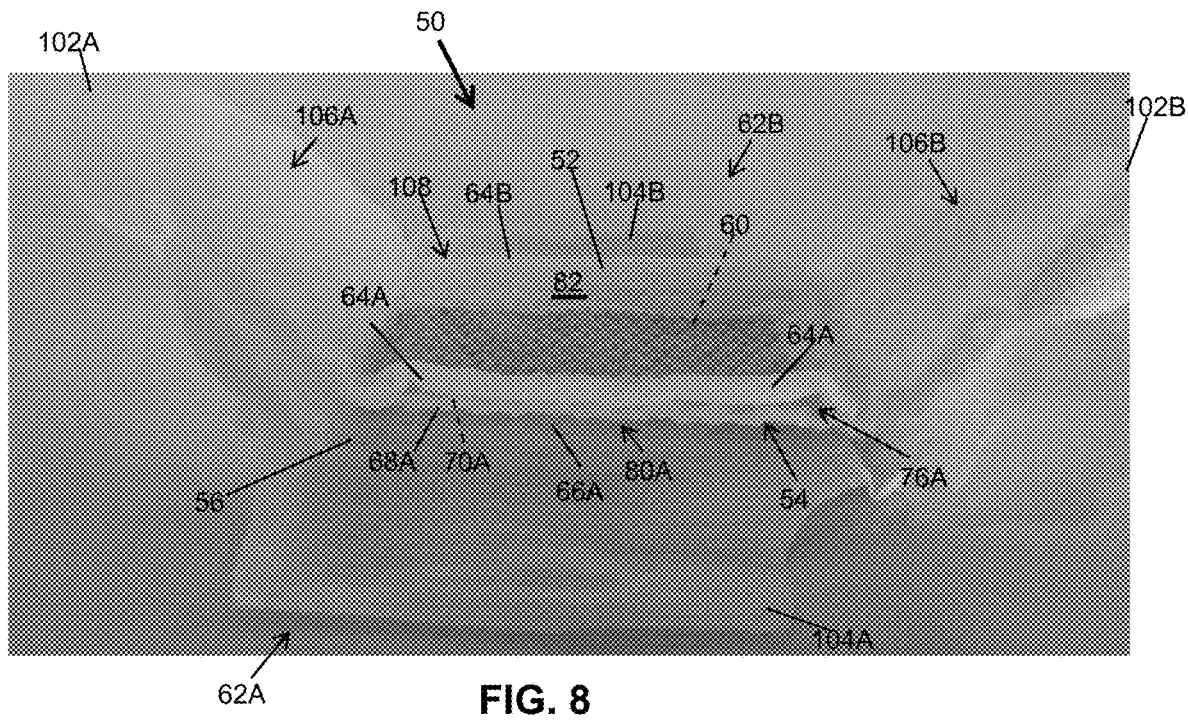
FIG. 8 is another top and lateral side perspective view of the sanitary article of FIG. 7.

FIGS. 7 and 8 show one of the lateral portions 64A of the top layer 52 which overlies and overs the middle lateral layer portion 68A containing the elastic 70A therein. Thus, the elastic 70A may be covered by a thin sheet 106A. The portion 68A is upwardly biased due to the elastic 70A therein, thereby upwardly lifting the lateral portion 64A upwardly. The lateral portion 64B is also shown to be lifted upwardly. Moreover, the elastics 70A and 70B pull the body sections 106A and 106B inwardly providing the concave and cup shapes to the article 50 shown in FIGS. 7 and 8. The foregoing provides for napkin 50 to maintain liquid on the pad section 108 in order to allow the liquid enough time to be absorbed by the core 60 and not spill therefrom. The portions 64A and 68A at lateral side 62A and the portions 64B and 68B at lateral side 62B prevent the liquid on section 108 from spilling over to layer 52. The upwardly portions 64A, 64B, 68A, 68B may also absorb excess liquid rising within section 108 and this absorbed liquid may flow downwards along the portions 64A, 64B, 68A, 68B towards the pad section 108.

Figure 9:
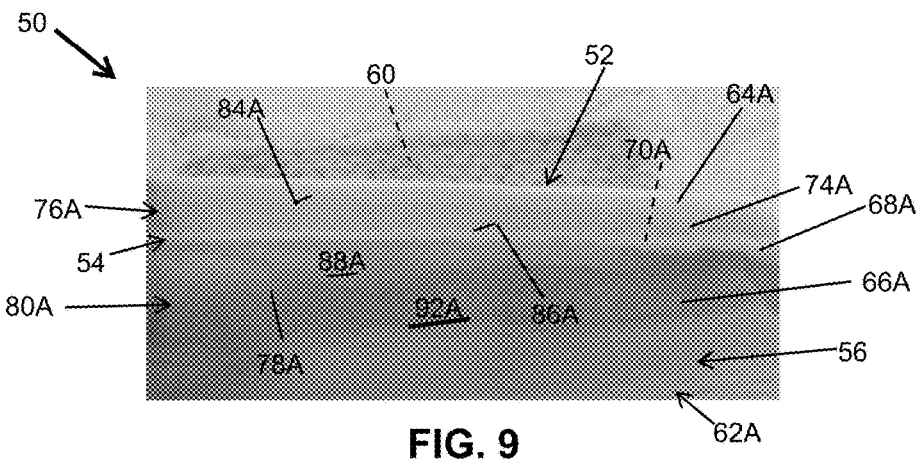
FIG. 9 is lateral side close-up view of the sanitary article of FIG. 7.

FIG. 9 shows the space 76A provided between the separate lateral portions 64A and 68B and the junction 74A. The undersurface 84A of portion 64A engages the top surface 86A of the portion 68A. The top surface 86A can be the complete top surface of the portion 68A. The foregoing is applicable to lateral side 62B mutatis mutandis.

Figure 10:
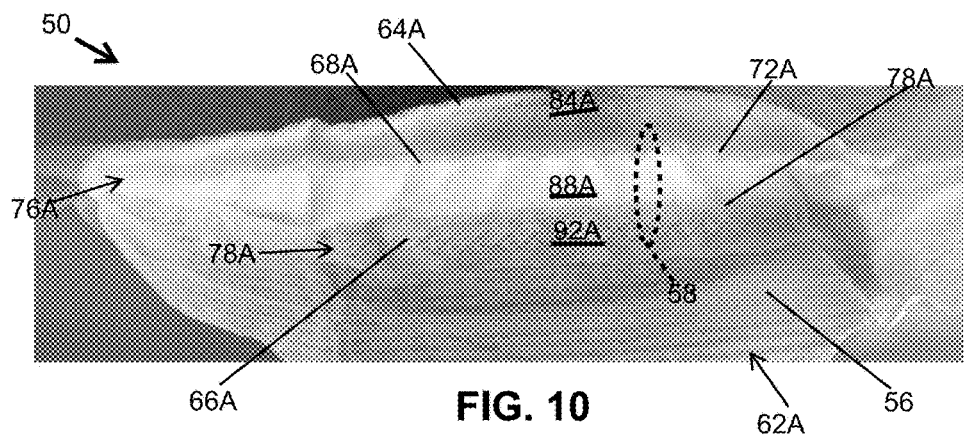
FIG. 10 is another lateral side close-up view of the sanitary article of FIG. 7.

FIGS. 9 and 10 show the space 80A between portions 68A and 66A and the junction 78A. The undersurface 88A of portion 68A may engage the inner surface 92A of portion 66A. The foregoing is applicable to lateral side 62B mutatis mutandis.

The spaces 76A, 76B and 80A and 80B allow for greater breathability to the article thus increasing comfort to the user. The spaces 76A and 76B allow for the V-shaped formation of portions 64A, 68A and junction 74A at side 62A and the V-shaped formation of portions 64B, 68B and junction 74B at side 62B. The V-shaped formation allows for providing lateral elastics which act as lateral barriers all the while avoiding the discomfort cause thereby by blocking the elastics from contacting the user.

Spaces 80A and 80B allow the layers 52 and 54 to have a concave and cup like shape and to take the form of the user's body in order to move therewith all the while allowing the layer 56 to have a convex form and move with the undergarment. Thus, creating laterally detached upper (layers 52 and 54) and lower (layer 56) parts that are attached at a mutual or common central core portion 58 thereof.

In an embodiment, the upper part comprises only layer 52 and thus layer 52 comprises the deformable and resilient members 70A and 70B. It is known in the art to provide elastics at the lateral margins of a pad. The elastics 70A and 70B can be covered by a sheet as described for the middle layer lateral portions 68A and 68B.

The various features described herein can be combined in a variety of ways within the context of the present disclosure so as to provide still other embodiments. Therefore, the various features of articles 10, 10' and 50 described herein including the various alternatives to each of the features provided herein can be combined in a variety of ways within the context of the disclosure. As such, the embodiments are not mutually exclusive. Moreover, the embodiments discussed herein need not include all of the features and elements illustrated and/or described and thus partial combinations of features can also be contemplated. Furthermore, embodiments with less features than those described can also be contemplated.

It is to be understood that the present disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation. Hence, although the present disclosure has been provided hereinabove by way of non-restrictive illustrative embodiments thereof, it can be modified, without departing from the scope, spirit and nature thereof and of the appended claims.

What is claimed is:

1. A sanitary article comprising:
   a longitudinal main body defining opposite longitudinal ends and opposite lateral sides and comprising an upper part, a lower part and an absorbent core therebetween attached together at a common central portion of the longitudinal main body, the upper part and the lower part being separated from each other at the lateral sides of longitudinal main body to define separate lateral upper part and lower part portions at each of the lateral sides;
   the upper part comprising a liquid pervious body contacting surface; and
   the lower part comprising a garment contacting surface;
   wherein each of the upper part lateral portions at each of the lateral sides comprises a top layer lateral portion and a middle layer lateral portion, the top layer lateral portion overlying the middle layer lateral portion and defining a space therebetween, the middle layer lateral portion overlying the lower part lateral portion and defining a space therebetween.

2. A sanitary article according to claim 1, wherein the lower part comprises a bottom layer defining bottom layer lateral portions at each of lateral sides.

3. A sanitary article according to claim 1, wherein the upper part comprises a top layer and wherein the upper part portions define top layer lateral portions.

4. A sanitary article according to claim 1, wherein the upper part lateral portions comprise respective resilient and deformable members for upwardly biasing the upper part lateral portions to prevent liquid on the body contacting surface from spilling therefrom.

5. A sanitary article according to claim 4, wherein the resilient and deformable members comprise elastics.

6. A sanitary article according to claim 4, wherein the upper part lateral portions comprise respective sheets for covering the resilient and deformable members.

7. A sanitary article according to claim 1, wherein each of the middle layer portions comprises a respective resilient and deformable member for upwardly biasing a respective top layer lateral portion to prevent liquid on the body contacting surface from spilling therefrom.

8. A sanitary article according to claim 7, wherein the resilient and deformable members comprise elastics.

9. A sanitary article according to claim 7, wherein each of the middle layer portions comprises respective sheets for covering the resilient and deformable members.

10. A sanitary article according to claim 1, wherein the lower part comprises laterally extending wings for being wrapped around an undergarment of a user.

* * * * *